US006960354B1

(12) United States Patent
Leigh et al.

(10) Patent No.: US 6,960,354 B1
(45) Date of Patent: Nov. 1, 2005

(54) MEMBRANE LIPID COMPOSITIONS

(75) Inventors: Steven Leigh, London (GB); Caroline Mary Thompson, London (GB); Mathew Louis Steven Leigh, London (GB)

(73) Assignee: Phares Technology BV, Amsterdam (NL)

( * ) Notice: Subject to any disclaimer, the term of this patent is extended or adjusted under 35 U.S.C. 154(b) by 0 days.

(21) Appl. No.: 09/890,770

(22) PCT Filed: Feb. 2, 2000

(86) PCT No.: PCT/GB00/00303

§ 371 (c)(1),
(2), (4) Date: Nov. 19, 2001

(87) PCT Pub. No.: WO00/45774

PCT Pub. Date: Aug. 10, 2000

(30) Foreign Application Priority Data

Feb. 4, 1999 (GB) .................................. 9902527

(51) Int. Cl.⁷ ...................... A61K 9/127; A61K 9/14; A61K 7/00
(52) U.S. Cl. ..................... 424/450; 424/401; 424/489; 424/490
(58) Field of Search ................. 424/450, 1.21, 424/9.321, 9.51, 417, 94.3, 401, 420, 489–502

(56) References Cited

U.S. PATENT DOCUMENTS

| 5,585,109 A | * | 12/1996 | Hayward |
| 5,614,215 A | * | 3/1997 | Ribier |
| 5,635,206 A | * | 6/1997 | Ganter et al. ............... 424/450 |
| 5,716,638 A | * | 2/1998 | Touitou |
| 5,811,119 A | * | 9/1998 | Mehta |
| 6,103,259 A | * | 8/2000 | Roux |

FOREIGN PATENT DOCUMENTS

| EP | 0 260 241 | | 3/1988 |
| FR | 2 627 388 | | 8/1989 |
| GB | 2 002 319 | * | 2/1979 |

* cited by examiner

Primary Examiner—Gollamudi S. Ksihore
(74) Attorney, Agent, or Firm—Wenderoth, Lind & Ponack, L.L.P.

(57) ABSTRACT

A composition in the form of a dry powder and which comprises: a) at least one membrane lipid, and b) at least one biologically active compound comprising a xanthine and/or a carboxylic acid, and which forms structured lipid assemblies when dispersed/dissolved in an aqueous medium. A method of preparing such a composition is also provided, together with a dispersion of structured lipid assemblies suspended in a solution of at least one biologically active compound and a method of preparing the same. The compositions and dispersions are suitable for use in creams and lotions for skin care.

8 Claims, 3 Drawing Sheets

MEMBRANE LIPID COMPOSITIONS

FIELD OF THE INVENTION

The present invention relates to membrane lipid compositions. More specifically, it relates to powder complexes and compositions comprising phospholipid and one or more biologically active compounds. The biologically active compound is a carboxylic acid, preferably a hydroxy (such as salicylate) or a keto carboxylic acid. Other biologically active compounds may optionally be included together with the carboxylic acid, for example a xanthine such as caffeine.

Powder compositions of the invention have the unique property to form dispersions comprising structured lipid assemblies (SLAs) suspended in a solution of the active compound. The compositions may be used to deliver the biologically active compound, such as a salicylate, to the deeper layers of the skin, more effectively and efficiently, with reduced irritation. By stabilising the active compounds in solution without solvents and strong surfactants, the invention is an improvement on prior art preparations containing salicylate. The compositions of this invention are employed in lotions, sprays and creams, etc in skin care and other applications.

BACKGROUND TO THE INVENTION

Cellulite is a fatty substance produced by fat cells (adipocytes) and deposited mainly under the thighs and buttocks which gives the skin an "orange peel" appearance. Two competing processes involving breakdown (lypolysis) and production (lypogenesis) of fat occur in the cells. In lypolysis, triglycerides are converted into free fatty acids and glycerol by the action of triglyceride lipases. This reaction is activated by cyclic AMP which converts the lipases into active forms. Lypolysis is controlled by phosphodiesterase, an enzyme which breaks down cyclic AMP and effectively prevents lypolysis. Xanthines, such as caffeine, theobromine and theophylline can inhibit phosphodiesterase and thereby promote lypolysis. These compounds are reported to be active topically and can also temporarily dehydrate cells, making the skin look and feel firmer. Not surprisingly, xanthines are used widely in skin care products and slimming aids to prevent cellulite from accumulating.

Caffeine is a methylxanthine which is a CNS stimulant and inhibitor of phosphodiesterase. It is a white crystalline solid, soluble 1:10 in hot water, but crystallises as fine needles on cooling. It is sparingly soluble in fixed oils and ethanol. The solubility in cold water is approximately 1:50. However it is soluble 1:10 in equal parts of ethanol and water. Topical preparations containing caffeine are commonly used in anti-cellulite treatments. The preparations are either hydro-alcoholic solution/gel or cream/lotion type products. There are problems relating to irritancy or reduced efficacy with both of these types of formulations. An effective amount of caffeine cannot be kept in solution without using large amounts of ethanol. If a large amount of ethanol is used, the solution dries rapidly, leaving a white powder on the skin after application. Creams and lotions are more cosmetically acceptable, but they are perceived to be less effective because of the smaller amount of caffeine that can be solubilised. Therefore there is a need for an aesthetic and cosmetically acceptable preparation containing an effective amount of caffeine which does not crystallise out, is non-irritant and does not dry out the skin.

Salicylic acid is used in topical applications as an exfoliating agent and to remove wrinkles from under the eyes, in low concentrations (<0.2/o), often as alkali salt. It is soluble in ethanol but only sparingly soluble in water. Salicylates, and in particular, salicylic acid is a skin irritant and it is usually combined with emollients in skin care products.

In this specification, the term phospholipid refers to at least one membrane lipid or, preferably, a mixture of membrane lipids comprising phosphatidyl choline (PC), phosphatidyl ethanolamine (PE), phosphatidyl inositol (PI), phosphatidic acid (PI) and/or phosphatidyl serine (PS). The definition includes diacyl phospholipids and their monoacyl equivalents, with either unsaturated or saturated hydrocarbon chain(s). Phospholipids are the most common examples of natural membrane lipids. They are the natural building blocks of cell membranes. Membrane lipids are essential for normal skin function. They protect the skin from irritants and alleviate the irritation. Therefore membrane lipids are commonly used in skin care preparations to confer emollient and protective functions and to control transepidermal water loss. Most commonly, they are used to form liposomes designed to carry active compounds. Liposomes are made up of one or more alternating bilayers which can sequester both oil soluble and water soluble compounds. Liposomes have poor long term storage stability, and therefore there are serious limitations in utilising liposomes to carry active compounds.

The present invention does not depend on liposome structure to entrap the active compound. It is not concerned with formation of liposomes, or with liposome entrapment. The compositions simply utilise phospholipids, particularly mixtures of diacyl and monoacyl phospholipids, to prepare easily dispersible powder compositions that form small structured lipid assemblies (SLAs) on contact with water. The SLAs may be vesicles, micelles, mixed micelles or often a heterogeneous mixture, depending on the types of phospholipid used. Typically, the SLAs have a diameter of between $0.05\mu$ to $1\mu$ (i.e. from 50 nm to 1000 nm). Surprisingly, it has been found that SLAs offer a valuable and effective source of natural membrane lipids that is convenient and easy to assimilate into the skin structure. The fact that the SLAs can also transport dissolved biologically active compounds is an unexpected bonus.

On p1651 of the 31st edition of Martindale The Extra Pharmacopoeia, it is disclosed that caffeine can be dissolved in concentrated solutions of alkali benzoates and salicylates. Caffeine is used orally in medicine as a CNS stimulant. It is also included in analgesics as the free base or as a water-soluble (e.g. citrate) salt. However, in skin care applications, the free base is mostly preferred due to its lipophilic properties.

There are many known caffeine preparations for anti-cellulite treatment. These contain a maximum of about 5% caffeine dissolved in ethanol or incorporated in the form of caffeine benzoate in creams and lotions.

FR-A-2627388 discloses a cream containing mucopolysaccharides, extracts of animal connective tissue and extracts of powdered cola nut (which contains caffeine), preferably together with liposomes. EP-A-260241 describes a composition comprising xanthine entrapped within liposomes. The products are intended strictly for inhalation and the presence of liposomes is required.

PCT application WO 95/34279 describes aqueous liposomal dispersions of phospholipids comprising a carboxylic acid or salicylic acid in the salt form that claim to be non-irritant and have skin beneficial properties. It would appear, from the examples disclosed, that the liposome suspensions are made from a pro-liposome composition disclosed in EP 0 158 441 B1.

SUMMARY OF THE INVENTION

The object of the present invention is two fold. Firstly, to provide a novel dry powder composition suitable for use in preparations for topical administration and which comprises at least one membrane lipid (e.g. phospholipid) with at least one biologically active compound (namely a carboxylic acid, e.g. alkali salicylate/salicylic acid), and which forms structured lipid assemblies (SLAs) when dispersed/dissolved in an aqueous medium, such as water. One or more other biologically active compounds, for example a xanthine (e.g. caffeine) may also be present. Secondly, to provide a stable dispersion of SLAs in situ, suspended in a solution of the biologically active compound(s) and that is suitable for use in preparations for topical administration. The dispersion may be made by using either the dry powder complex or by incorporating (dispersing/dissolving) the components thereof individually in water or other aqueous medium. Creams, gels, lotions, sprays and other preparations formulated for topical administration may be prepared from the dispersion or suspension accordingly.

In the compositions of this invention which contain them both, the efficacy of caffeine is enhanced because it is in molecular solution with the salicylate. Most importantly, the invention harnesses the properties of phospholipids to improve the bioavailability and reduce the irritancy of biologically active compounds, in a physically stable complex. Furthermore, the method of this invention avoids the use of solvents or harsh surfactants which can irritate and damage the skin. This represents a significant improvement on prior art preparations containing a xanthine and a carboxylic acid. Compositions comprising phospholipid, caffeine and/or salicylate in a dry powder complex have not been disclosed in the prior art.

DESCRIPTION OF PREFERRED EMBODIMENTS

Figure 1A:
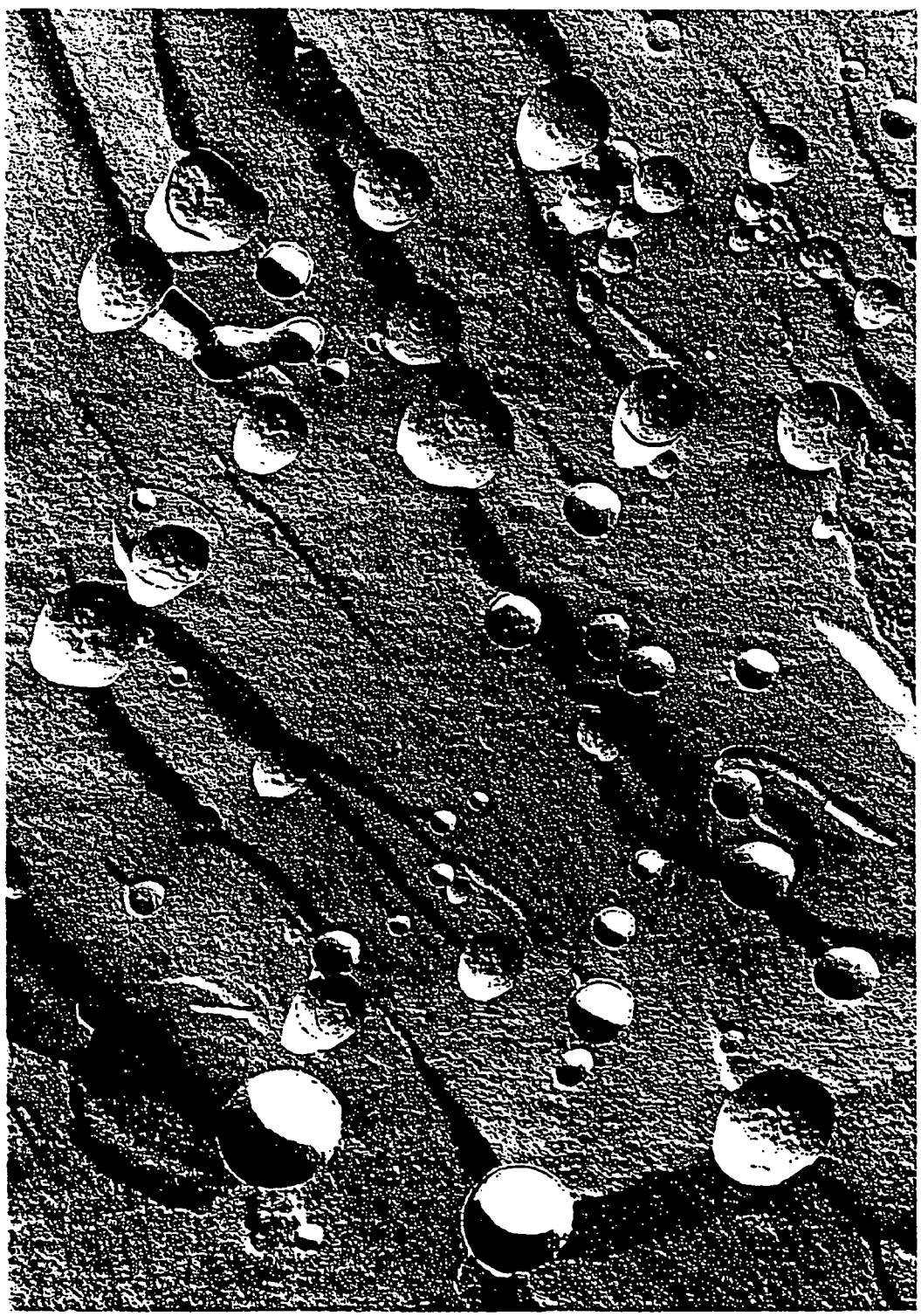
FIG. 1A depicts an electron micrograph of a suspension of the powdered composition of the present invention in water.

A preferred embodiment of the invention is a powder composition comprising the components in a homogeneous mixture. The preferred xanthine is caffeine as the free base, but other xanthines such as aminophilline, theophylline and theobromine may also be used. The proportion of caffeine in the powder complex is preferably between 10% to 80%, more preferably between 40% to 70%, by weight.

Sodium salicylate/salicylic acid, a β-hydroxycarboxylic acid, is the preferred carboxylic acid but other alkali salicylates or benzoates may be used. Benzoates tend to be more sensitising and should therefore be used with caution. The amount of sodium salicylate by weight in the powder mixture is preferably between 10% to 50%, more preferably between 20% to 40%. In addition to or in place of salicylates, α-hydroxycarboxylic acids, e.g. glycollic acid, lactic acid, citric acid, tartaric acid, maleic acid or mandelic acid, and/or α-ketocarboxylic acids, e.g. pyruvic acid, including their salt forms may be used in about the same proportions, i.e. about 10% to about 50% by weight, with the pH of the final preparation adjusted to between pH 5 to 7.5, so as to give maximum performance and minimum irritancy. The α-hydroxy carboxylic acids are found in fruit extracts and are known as "fruit acids". They are commonly used in anti-wrinkle preparations due to their keratolytic and antioxidant properties. It will be understood that the products of this invention may contain one, two, three or more biologically active compounds.

According to one preferred embodiment of the invention, at least one carboxylic acid or salt, eg, salicylate, is used in combination with the lipid to counteract the irritant potential of the fruit acids. These compositions are particularly suitable in anti-wrinkle skin care preparations.

Where only two components, e.g. phospholipid and one carboxylic acid or acid salt, are present in the powder composition, the weight ratio of lipid to biologically active compound is 20:1 to 1:20, preferably 10:1 to 5:1, with the proviso that there is sufficient lipid in the powder mixture to yield SLAs, when the powder mixture is dispersed in water at about 60° C.

The second essential component is a membrane lipid, and this may include natural, hydrogenated and synthetic phospholipids, glycolipids and polyglycerol esters. Blends of diacyl or monoacyl phospholipid available commercially as lecithin and enzyme hydrolysed lecithin, with a total phospholipid content of at least 60%, are preferred. Diacyl phospholipids, e.g. PC, tend to form SLAs which may be bilayered lamellae structures with an average diameter of about 1 μin water, whilst monoacyl phospholipids (MAPC) form micelles that are about 50 nm average diameter. Mixed micelle systems are formed by combinations of PC and MAPC and the average particle size is somewhere in between the diameters quoted above. Most preferably, the phospholipids are in particulate or granular form. The quantity of lipid in the dry powder mixture varies between 5% to 70%, most preferably between 10% to 50%. A combination of unsaturated lipid with low phase transition temperature (Tc) and hydrogenated lipid with higher Tc is preferred to obtain complexes with optimum properties.

There are several benefits in using phospholipids in the invention. In skin care products, they can replace natural lipid and function as natural moisturisers, counteract the dehydrating effect of caffeine, and alleviate the irritant potential of the fruit acids. Phospholipids are also known to increase the bioavailability of biologically active compounds. Furthermore, phospholipids stabilise the formulations, preventing any mild crystal growth of e.g. caffeine, if the preparations are stored at low temperatures. This effect can be seen when two formulations are prepared, one containing a high level of caffeine without lipid, the other containing caffeine and lipid complex. When stored at 4° C., crystals develop much faster in the preparation without lipid. Phospholipids are natural emulsifiers and can help stabilise up to 40% of an oil and thereby reduce the amount of ethoxylated emulsifiers. A further advantage of the invention is that the phospholipid helps to bind and prevent segregation of the components in the powder mixture, particularly during storage and transport.

The powder compositions may be prepared by dissolving/dispersing all the components in a suitable solvent, e.g. ethanol, aqueous ethanol solutions or chloroform and removing the solvent to obtain a solid complex that can be pulverised. Alternatively, all the components may be simply mixed or milled together to obtain a homogeneous and uniform powder mixture. This offers a convenient and efficient means to utilise caffeine and/or salicylate in a form which can be incorporated into different types of formulations. The powder mixture is simply added to water or other aqueous medium to obtain, in situ, a soluble caffeine and/or salicylate complex in a dispersion of lipid particles, free from ethanol. The suspension may be used as a sprayable lotion or it may be used to prepare creams and lotions that can additionally contain up to 40% of an oil.

The lipid-caffeine powder complex is a homogeneous composition with a mean particle size between 0.1 mm to about 5 mm in diameter. Preferably, the mean diameter is about 200µ to 500µ. The compositions have good storage stability and can be kept for extended periods until required.

In a further embodiment of the invention, the individual components, namely phospholipid and the biologically active compound(s) e.g. caffeine and salicylate, are added separately in pre-weighed amounts, to water or other aqueous medium. The resulting dispersion of SLAs can be used in the preparation of a cream or a lotion. The order is not critical, although preferably, the salicylate should be added first, followed by the caffeine or other xanthine. The lipid, which should preferably be in particulate form, is added last to the solution, with stirring, at an elevated temperature below about 60° C. The phospholipids additionally help to keep the caffeine/salicylate in solution, most likely in a molecular complex. The mol ratio of caffeine to salicylate in the solution is between 1:1 to 1:4, preferably about 1:2. There is no strict limit to the ratio of caffeine to lipid, but preferably it should lie within the range 20:1 to 1:20, preferably 10:1 to 5:1.

The invention will be further described in the following examples. All percentages are by weight unless otherwise indicated.

EXAMPLE 1

| | |
|---|---|
| Caffeine | 52.6% |
| Salicylic acid (Na salt) | 26.3% |
| *Phospholipid | 21.1% |

*Mixture of suitable lipid blends, containing a minimum of 60% total phospholipids comprising PC, PE, PA, PI, and glycolipids in particulate form. In the above example the lipid blend was made up of a 1:2 mixture of hydrogenated and unsaturated lipids.

Method: 500 gm of the lipid-caffeine powder complex was prepared in the laboratory by grinding all the components in a mortar and pestle until a homogeneous and uniform powder composition was obtained. One gm of the powder composition dispersed in 10 ml of water at 60° C. to yield a solution of caffeine and SLAs in suspension, comprising vesicular structures of about 1 µZ average diameter, as seen in the accompanying electron micrograph of FIG. 1A.

EXAMPLE 2

| | |
|---|---|
| Caffeine | 58.8% |
| Salicylic acid (Na salt) | 29.4% |
| *Phospholipid | 11.8% |

*Similar blend as in Example 1.

10 gm of the components was dissolved in 90% ethanol at about 50° C. in a closed container. The ethanol was evaporated off to obtain a hard powder lump which could be comminuted to a free flowing powder of about 500 micron average diameter.

EXAMPLE 3

| | |
|---|---|
| Caffeine | 64.8% |
| Salicylic acid (Na salt) | 24.9% |
| *Phospholipid | 10.3% |

*Enyme modified lecithin containing about 65% MAPC and 15% PC.

Figure 1B:
FIG. 1B depicts an electron micrograph of a solution of the powdered composition of the present invention in water.

10 kg of the lipid-caffeine powder complex was prepared by coarse mixing, followed by size reduction through a screen in a hammer mill, to obtain a free flowing uniform powder composition. Alternatively, the three components could have been dissolved in ethanol-water solution and dried to a powder. One gm of the powder dispersed in 10 ml of warm water to give a clear micellar solution of caffeine and SLAs, as seen in the electron micrograph of FIG. 1B (where no vesicular structures can be discerned).

EXAMPLE 4

| | |
|---|---|
| Salicylic acid (Na salt) | 50.0% |
| *Phospholipid | 50.0% |

*Hydrogenated lipid containing about 60% of total phospholipids and glycolipids.

The two components were co-milled to obtain a free flowing uniform lipid-salicylate powder composition that readily disperses in water at about 60° C. with minimum agitation, to form a homogeneous dispersion of discrete SLAs and dissolved salicylate. In place of salicylate, one or more alpha hydroxycarboxylic acids (AHA) e.g. citric acid or maleic acid or their salt forms may be used.

The invention also relates to the use of the aforementioned lipid powder compositions for preparing suspensions, lotions and creams containing caffeine and/or a carboxylic acid/salt. Typical examples of the preparations are further described below.

EXAMPLE 5

The lipid-caffeine powder from Example 1 was used to prepare an oil in water (o/w) cream.

| | |
|---|---|
| Lipid-caffeine complex | 7% |
| Emulgade SEV | 5% w/w |
| Cetyl alcohol | 2% |
| Dicaprylyl ether | 4% |
| Oleyl erucate | 1% |
| Decyl oleate | 2% |
| Cocoglycerides | 3% |
| Glycerol | 3% |
| Preservative | 0.2% |
| Fragrance | 0.2% |
| Water | ad 100% |

Figure 2A:
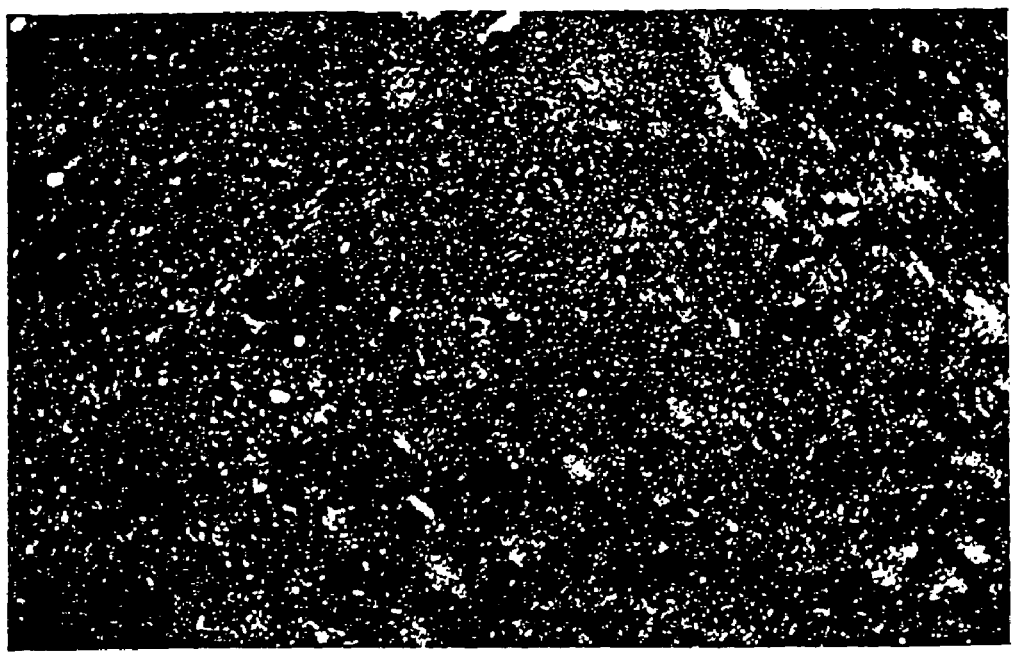
FIG. 2A depicts a photograph of a cream of the present invention, as seen under a light microscope at a magnification of about 100×.
Figure 2B:
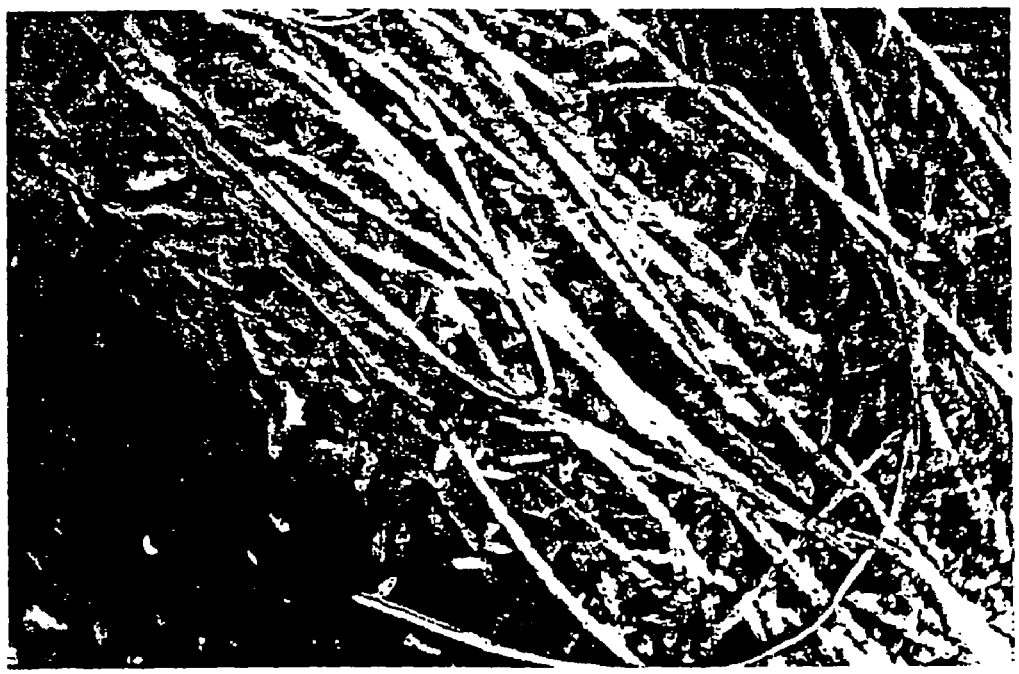
FIG. 2B depicts a similar photograph of a control cream."

The emulsifier (Emulgade) was obtained from Henkel. The lipid-caffeine powder from Example 1 was dispersed in about half the total amount of water at about 60° C. The emulsifier and waxes were melted in the mixture of oils heated to about 65° C. and added to the aqueous suspension of caffeine, with stirring to form a cream. The rest of the water at 60° C. was added to obtain an o/w lipid-caffeine cream. The cream was homogenised and cooled to room temperature. It was packed into jars. After storage for 30 days at 0° C. and 45° C., the cream was examined at room temperature, for crystal growth. No crystals can be seen under a light microscope (at magnification of about ×100), as shown in FIG. 2A (which shows a sample of the cream according to this example after storage at 0° C. for 30 days). FIG. 2B shows a sample of a cream prepared as a control (containing caffeine but no lipid) after storage at 0° C. for 30 days; crystals have clearly developed.

EXAMPLE 6

The lipid-caffeine powder complex from Example 2 was used to prepare the gel formulation in this example.

| | |
|---|---|
| Lipid-caffeine complex | 6% |
| Glycerol | 3% |
| Carbopol 940 | 0.4% |
| Permulant TR-1 | 0.2% |
| Cetearyl isononanate | 3% |
| Tocopherol acetate | 0.05% |
| Preservative | 0.2% |
| Fragrance | 0.2% |
| Water | ad 100% |

The Carbopol (a gelling agent) and Permulant (a thickener) were hydrated and dissolved in about half quantity of water at about 60° C., with high speed stirring, to obtain a lump free solution. The rest of the ingredients, except for the lipid-caffeine complex and the fragrance, were added. The lipid-caffeine complex was dispersed in the rest of the water at about 65° C. to form a homogeneous lipid suspension and added to the Carbopol solution. The suspension was adjusted to pH 6.5–7.0 to obtain a gel preparation comprising discrete SLAs and solubilised caffeine.

EXAMPLE 7

This is an example of a simple lotion containing SLAs and solubilised caffeine prepared from the lipid-caffeine complex according to Example 3.

| | |
|---|---|
| Lipid-caffeine complex | 8% |
| Preservative | 0.2% |
| Fragrance | 0.2% |
| Water | ad 100% |

The lipid-caffeine powder was added to water at ambient temperature containing the preservative, with mild agitation. A totally transparent micellar solution of SLAs with Z average diameter of below about 60 nm was obtained using a Malvern autosizer. The fragrance was added last.

In place of the lipid-caffeine complex from Example 3, two gm of the lipid-salicylate complex from Example 4 was added to the water containing the preservative at about 65° C., with agitation, to prepare a translucent lotion containing SLAs suspended in caffeine solution. The fragrance was added at room temperature. The Z average particle diameter of the SLAs was about 1μ, using a Malvern autosizer laser.

The powder complexes in Examples 1 to 4 are typical examples. Similar powder complexes may be prepared by using different blends of phospholipids and other xanthines and carboxylic acids. Alternatively, the xanthine may be omitted and a powder complex comprising phospholipid and one or more fruit acids or one or more α-ketocarboxylic acids may be obtained using similar methods. In this case, the amount of fruit acid used in the powder mixture may vary from 10% to 50% by weight. The resultant powder compositions may be formulated into creams and lotions which are typically shown in Examples 5 to 7.

What is claimed is:

1. A composition in the form of a homogenous dry powder mixture wherein the mean particle size of the powder composition is between 0.1 to 5 mm in diameter consisting essentially of:
   a) at least one membrane lipid in an amount of from 5% to 70% by weight,
   b) at least one biologically active compound that is a carboxylic acid selected from the group consisting of an α-hydroxycarboxylic acid, a β-hydroxycarboxylic acid and/or an α-ketocarboxylic acid, and
   c) at least one biologically active compound that is a xanthine selected from the group consisting of caffeine, aminophilline, theophylline and theobromine,
and which is prepared by mixing or milling together said components to obtain the dry powder mixture,
and which forms structured lipid assemblies when dispersed/dissolved in an aqueous medium.

2. The composition as claimed in claim 1, wherein said membrane lipid comprises a phospholipid or mixture of phospholipids.

3. The composition as claimed in claim 1, wherein said biologically active compound is salicylic acid or a pharmaceutically acceptable salt thereof in an amount of from 10% to 50% by weight.

4. The composition as claimed in claim 1, wherein the xanthine is caffeine and is present in an amount of from 10% to 80% by weight.

5. The composition as claimed in claim 1, wherein the proportion of said membrane lipid to said biologically active compounds is from 1:20 to 20:1 by weight.

6. A method of preparing a composition in the form of a homogenous dry powder mixture the mean particle size of the composition being between 0.1 to 5 mm and which composition consisting essentially of:
   a) at least one membrane lipid in an amount of from 5% to 70% by weight, b) at least one biologically active compound that is a carboxylic acid selected from the group consisting of an α-hydroxycarboxylic acid, a β-hydroxycarboxylic acid and/or an α-ketocarboxylic acid, and
   c) at least one biologically active compound that is a xanthine selected from the group consisting of caffeine, aminophilline, theophylline and theobromine, and which forms structured lipid assemblies when dispersed/dissolved in an aqueous medium, which method comprises mixing or milling together the components to produce a homogeneous dry powder mixture.

7. A composition in the form of a homogeneous dry powder mixture which is prepared according to the method of claim 6.

8. The composition as claimed in claim 1, wherein the xanthine is caffeine.

* * * * *